(12) United States Patent
Merdan

(10) Patent No.: US 6,685,679 B2
(45) Date of Patent: Feb. 3, 2004

(54) INTERLOCKING METAL SHAFT

(75) Inventor: Kenneth M. Merdan, Greenfield, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 195 days.

(21) Appl. No.: 09/731,514

(22) Filed: Dec. 6, 2000

(65) Prior Publication Data

US 2002/0068912 A1 Jun. 6, 2002

(51) Int. Cl.$^7$ .......................... A61M 25/00; A61M 5/00
(52) U.S. Cl. ........................................ 604/264; 604/282
(58) Field of Search ............................. 600/16; 604/95, 604/282, 264; 623/1.37

(56) References Cited

U.S. PATENT DOCUMENTS

| | | | |
|---|---|---|---|
| 4,265,848 A | 5/1981 | Rusch | 264/130 |
| 4,283,447 A | 8/1981 | Flynn | 428/36 |
| 4,596,563 A | 6/1986 | Pande | 604/264 |
| 4,636,346 A | 1/1987 | Gold et al. | 264/139 |
| 4,657,024 A | 4/1987 | Coneys | 128/658 |
| 4,762,129 A | 8/1988 | Bonzel | 606/194 |
| 5,156,785 A | 10/1992 | Zdrahala | 264/108 |
| 5,221,270 A | 6/1993 | Parker | 604/282 |
| 5,308,342 A | 5/1994 | Sepetka et al. | 604/282 |
| 5,316,706 A | 5/1994 | Muni et al. | 264/25 |
| 5,329,923 A | 7/1994 | Lundquist | 128/642 |
| 5,334,171 A | 8/1994 | Kaldany | 604/282 |
| 5,358,493 A | 10/1994 | Schweich, Jr. et al. | 604/264 |
| 5,381,782 A | 1/1995 | DeLaRama et al. | 128/4 |
| 5,454,787 A | 10/1995 | Lundquist | 604/95 |
| 5,477,856 A | 12/1995 | Lundquist | 128/642 |
| 5,507,751 A | 4/1996 | Goode et al. | 606/108 |
| 5,507,995 A | 4/1996 | Schweich, Jr. et al. | 264/293 |
| 5,573,520 A | 11/1996 | Schwartz et al. | 604/282 |
| 5,599,319 A | 2/1997 | Stevens | 604/264 |
| 5,685,868 A | 11/1997 | Lundquist | 604/280 |
| 5,897,537 A * | 4/1999 | Berg et al. | 604/282 |
| 5,921,956 A * | 7/1999 | Grinberg et al. | 604/95 |
| 6,007,478 A * | 12/1999 | Siess et al. | 600/16 |
| 6,017,335 A | 1/2000 | Burnham | 604/282 |
| 6,022,343 A | 2/2000 | Johnson et al. | 604/526 |
| 6,152,957 A * | 11/2000 | Jang | 623/1.37 |
| 6,168,588 B1 * | 1/2001 | Wilson | 604/525 |

FOREIGN PATENT DOCUMENTS

| | | | |
|---|---|---|---|
| DE | 4104092 | 2/1991 | |
| DE | 4104092 * | 8/1991 | A61B/17/34 |
| EP | 0 680 351 Ba | 9/1992 | |
| EP | 0 608 853 A2 | 1/1994 | |
| FR | 2713492 | 12/1993 | |
| JP | 8257128 | 10/1996 | |
| JP | 8308933 | 11/1996 | |
| WO | WO 99/11313 | 3/1999 | |

* cited by examiner

*Primary Examiner*—Henry Bennett
*Assistant Examiner*—Sabrina Dagostino
(74) *Attorney, Agent, or Firm*—Crompton, Seager & Tufte LLC (57) ABSTRACT

The present invention relates generally to catheters for performing medical procedures including percutaneous transluminal coronary angioplasty. Moreover, the present invention relates to catheters with improved shaft designs, particularly improved flexibility, pushability, torquability, and limited kinking. A catheter shaft, comprising an elongate support member, a longitudinal axis, a sheath disposed about the elongate support member, and at least one gap along the longitudinal axis is disclosed. The gap defines a first edge and a second edge. The gap may comprise a variable taper. Alternately, a first projection extends from the first edge and a second projection extends from the second edge. The projections may comprise interlocking rounded projections, non-interlocking projections, interlocking projections, modified projections of differing shapes, and combinations thereof.

14 Claims, 12 Drawing Sheets

INTERLOCKING METAL SHAFT

FIELD OF THE INVENTION

The present invention relates generally to catheters for performing medical procedures including percutaneous transluminal coronary angioplasty. More particularly, the present invention relates to catheters with improved shaft designs.

BACKGROUND OF THE INVENTION

The use of intravascular catheters has become an effective method for treating many types of vascular disease. In general, an intravascular catheter is inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular catheters include percutaneous transluminal angioplasty (PTA) and percutaneous transluminal coronary angioplasty (PTCA).

Intravascular catheters are commonly used in conjunction with a guidewire. A guidewire may be advanced through the patient's vasculature until it has reached a target location. Once in place, a catheter may be threaded onto the guidewire and urged distally until the distal end of the catheter reaches a target location.

Intravascular catheters adapted for use with a guidewire typically are classified as over-the-wire (OTW) or single operator exchange (SOE). An OTW catheter includes a guidewire lumen extending from the distal tip of the catheter to the proximal end of the catheter. When intravascular catheters are used, it is common for physicians to remove one catheter and exchange it for another. While exchanging catheters, the guidewire must be held in place so as to keep its distal end near the target area. A portion of the guidewire is typically grasped by the physician in order to withdraw the first catheter while maintaining the distal end of the guidewire in the desired position. To properly anchor the guidewire, a portion of the guidewire must be exposed at all times so it is available for the physician to grasp. In the case of an OTW catheter, this requires that the length of the guidewire extending beyond the patient's body be longer than the catheter. Consequently, in many cases intravascular catheters are longer than 200 cm or require guidewire extensions to facilitate exchange. Correspondingly, there may be more than 200 cm of wire extending from the patient. Managing this length of wire during a catheter exchange procedure is awkward, and typically requires more than one person. Additionally, contamination must be avoided by assuring that the guidewire is not dropped from the sterile field.

SOE catheters were developed in response to difficulties encountered when exchanging OTW catheters. Accordingly, SOE catheters have a relatively short guidewire lumen relative to the length of the catheter. Therefore, the length of guidewire extending beyond the body of the patient need only be slightly longer than the guidewire lumen of the catheter. The physician may anchor or hold the guidewire as the first catheter is removed from the body with the exchange occurring over the shorter guidewire lumen. The guidewire lumen of an SOE catheter typically includes a distal guidewire port disposed at the distal tip of the catheter and a proximal guidewire port disposed proximally of the distal end of the catheter.

When in use, intravascular catheters enter a patient's vasculature at a convenient location and then are urged to a target region. Once the distal portion of the catheter has entered the patient's vascular system the physician may urge the distal tip forward by applying longitudinal forces to the proximal portion of the catheter. For the catheter to effectively communicate these longitudinal forces it is desirable that the catheter have a high level of pushability and kink resistance particularly near the proximal end.

Frequently the path taken by a catheter through the vascular system is tortuous, requiring the catheter to change direction frequently. In some cases, it may even be necessary for the catheter to double back on itself. In order for the catheter to conform to a patient's tortuous vascular system, it is desirable that intravascular catheters be very flexible, particularly near the distal end.

Further, while advancing the catheter through the tortuous path of the patients vasculature, physicians often apply torsional forces to the proximal portion of the catheter to aid in steering the catheter. Torsional forces applied on the proximal end must translate to the distal end to aid in steering. It is therefore desirable that the proximal portion of an intravascular catheter have a relatively high level of torquability to facilitate steering.

The need for this combination of performance features is often addressed by manufacturing a catheter that has two or more discrete tubular members having different performance characteristics. For example, a relatively flexible distal section may be connected to a relatively rigid proximal section. When a catheter is formed from two or more discrete tubular members, it is often necessary to form a bond between the distal end of one tubular member and the proximal end of another tubular member.

An approach used to enhance pushability and torquability of intravascular catheters is to construct the proximal end from hypodermic tubing, or a "hypotube". While a hypotube can add significant pushability and torquability to an intravascular catheter due to its intrinsic strength and rigidity, it can kink.

A need, therefore, exists for the manufacturing of SOE intravascular catheters to include shaft designs that maintain pushability, flexibility, and torquability while limiting the untoward properties of using a hypotube.

SUMMARY OF THE INVENTION

The present invention relates generally to catheters for performing medical procedures including percutaneous transluminal coronary angioplasty. More particularly, the present invention relates to catheters with improved shaft designs. Preferably, the catheter shaft comprises an elongate support member with proximal and distal ends, at least one gap within the elongate support member. In a preferred embodiment of the current invention, a sheath is disposed about the elongate support member.

In a preferred embodiment of the current invention, the gap defines a first edge and a second edge. Preferably, a first projection extends from the first edge and a second projection extends from the second edge. In an exemplary embodiment, the first projection and the second projection overlap. According to a preferred embodiment, the first edge and the second edge may further comprise additional projections.

In an exemplary embodiment of the current invention, a gap within the elongate support member is used to improve its properties. Preferably, the gap improves flexibility while retaining the desired level of pushability and torquability. The gap within the elongate support member may be formed by a number of methods. The methods of forming a gap may include, but are not limited to, cutting (for example laser cutting), sawing, and electrochemical masking.

In a particular embodiment of the current invention, a gap defines a first edge and a second edge. Preferably, the gap comprises a variable taper wherein the gap changes from the proximal to distal end. By introducing a taper, the level of flexibility may vary between proximal and distal ends. For example, the taper may result in a gap that is greater near the distal end. This could result in greater flexibility near the distal end of the catheter.

In an alternative embodiment of the current invention, the first projection and the second projection are interlocking. In an exemplary embodiment, the first projection is substantially rounded. By interlocking the projections, the elongate support member may retain pushability and torquability while increasing flexibility. Further, altering the shape of the projections can enhance desired flexibility changes throughout the elongate support member. For example, a rounded projection can vary in size along the longitudinal axis of the elongate support member. A specific example may include larger projections near the proximal end and smaller projections near the distal end. In this example, the smaller projections near the distal end may increase flexibility near the distal end of the elongate support member.

Additionally, the amount of gap formed between a plurality of projections can vary. For example, the gap between interlocking surfaces may be uniformly altered in differing embodiments. In this example, an elongate support member could be constructed that has increased gap length between interlocking projections at a proximal or distal end that may result in altered flexibility.

Further, the gaps formed between interlocking surfaces may vary along the longitudinal axis of the elongate support member. For example, the gap length may be greater near the distal end of the elongate support member. This may result in increased catheter shaft flexibility near the distal end.

Additionally, in alternative embodiments of the current invention, the elongate support member may comprise more than one piece. This multi-piece configuration may add beneficial properties to the catheter shaft including, but not limited to, increased flexibility, increased kink resistance, pushability, and torquability. One skilled in the art would be familiar with the advantages of manufacturing a multi-piece configuration that would be appropriate for multiple embodiments of the current invention. Further, the methods for producing a multi-piece elongate support member would be familiar to one skilled in the art.

In an alternative embodiment of the current invention, the first projection and the second projection are non-interlocking. The projections could manifest in a multiplicity of shapes according to differing embodiments of the current invention.

In an preferred embodiment of the current invention, the gap length for non-interlocking projections can be varied. For example, a projection may have a relatively longer gap in the longitudinal direction (along the longitudinal axis) of the catheter shaft and a relatively shorter gap in the direction perpendicular to the longitudinal axis of the elongate support member. In this example, the catheter shaft may have increased circumferential flexibility while allowing little axial movement. Multiple embodiments of the current invention can be derived that incorporate varied gaps along projections.

Additionally, the amount of gap formed between a plurality of projections can vary. For example, the gap between non-interlocking projections may be uniformly altered in differing embodiments. In this example, an elongate support member could be constructed that has increased gap length between non-interlocking projection near a proximal end or a distal end that may result in altered flexibility.

In an alternative embodiment of the current invention, the first projection and the second projection may comprise differing shapes. In multiple embodiments of the current invention, the projections could also have varying size and gap length as illustrated above. Further, multiple embodiments can be derived that incorporate varied gaps between projections as illustrated above. Similar alterations can be derived for modified projections of differing shapes.

In an alternative embodiment of the current invention, the first edge and the second edge defines a tapered and a non-tapered region. The taper forms a gap that changes from the proximal to the distal end. By introducing both a taper and a non-tapered region, the level of flexibility can vary between proximal and distal ends. For example, a non-tapered region may result in a less flexible region near the proximal end of the catheter and the taper may result in a gap that is greater near the distal end. This could result in greater flexibility near the distal end of the catheter.

DETAILED DESCRIPTION OF THE PREFERRED EMBODIMENTS

Figure 1:
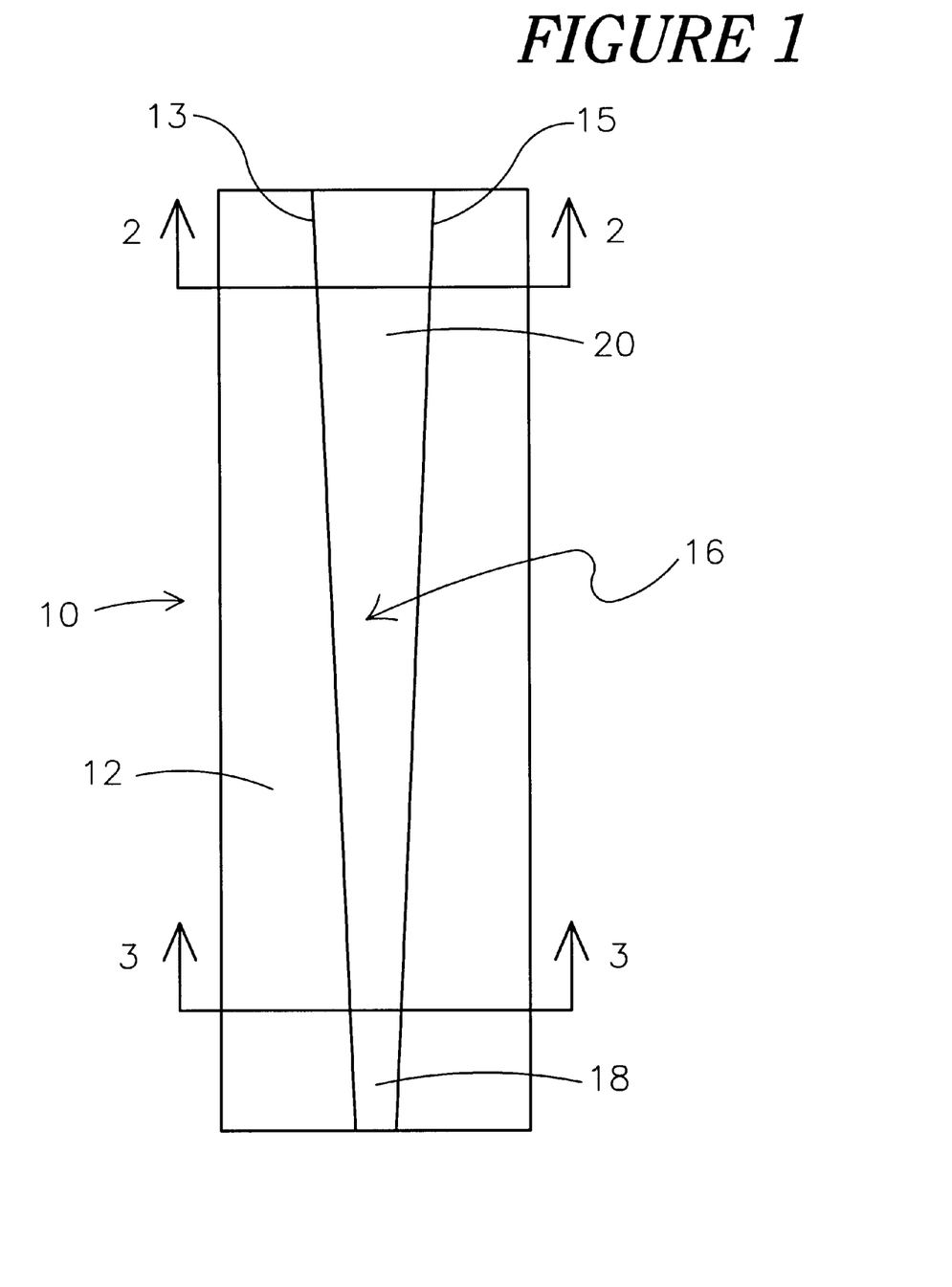
FIG. 1 is a longitudinal view of a catheter shaft with an elongate support member comprising a gap defining a first edge and a second edge, wherein the gap comprises a taper.

Referring now to the drawings wherein like reference numerals indicate like elements throughout the several views, FIG. 1 is a longitudinal view of a catheter shaft with an elongate support member comprising a gap that defines a first edge and a second edge, wherein the a gap comprises a taper. Catheter shaft 10 comprises elongate support member 12 disposed within a sheath (not shown in FIG. 1, see FIG. 2). Elongate support member 12 can be manufactured from multiple materials including, but not limited to, thermoplastics, high performance engineering resins, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), metal, stainless steel, metal alloys, nickel alloys, and nickel titanium alloys. Additionally, elongate support member 12 can be formed from hollow cylindrical stock or a flat sheet that is cut and rolled.

A sheath disposed about elongate support member 12 can be manufactured from materials including, but not limited to, thermoplastics, high performance engineering resins, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, or perfluoro(propyl vinyl ether) (PFA). One skilled in the art would be able to determine which material to use for manufacturing a sheath for a catheter according to multiple embodiments of the current invention.

A gap within elongate support member 12 defines a first edge 13 and a second edge 15, and comprises a taper 16 between the proximal and distal ends. Preferably taper 16 varies between proximal and distal ends. Taper 16 comprises a narrower gap 18 and a wider gap 20. By introducing taper 16, the level of flexibility may vary between proximal and distal ends. For example, taper 16 may result in a gap that is greater near the distal end of the catheter shaft. This could result in greater flexibility near the distal end of the catheter. Cross-sections cut through elongate support member 12 include line 2—2 (shown in FIG. 2) and line 3—3 (shown in FIG. 3).

In multiple embodiments of the current invention, at least one gap is formed within the elongate support member to improve its properties. Preferably, the gap improves flexibility while retaining the desired level of pushability and torquability. The shaft may be cut by a number of methods, which are known to one skilled in the art. The methods of cutting may include, but are not limited to, laser cutting, sawing, and electrochemical masking.

Figure 2:
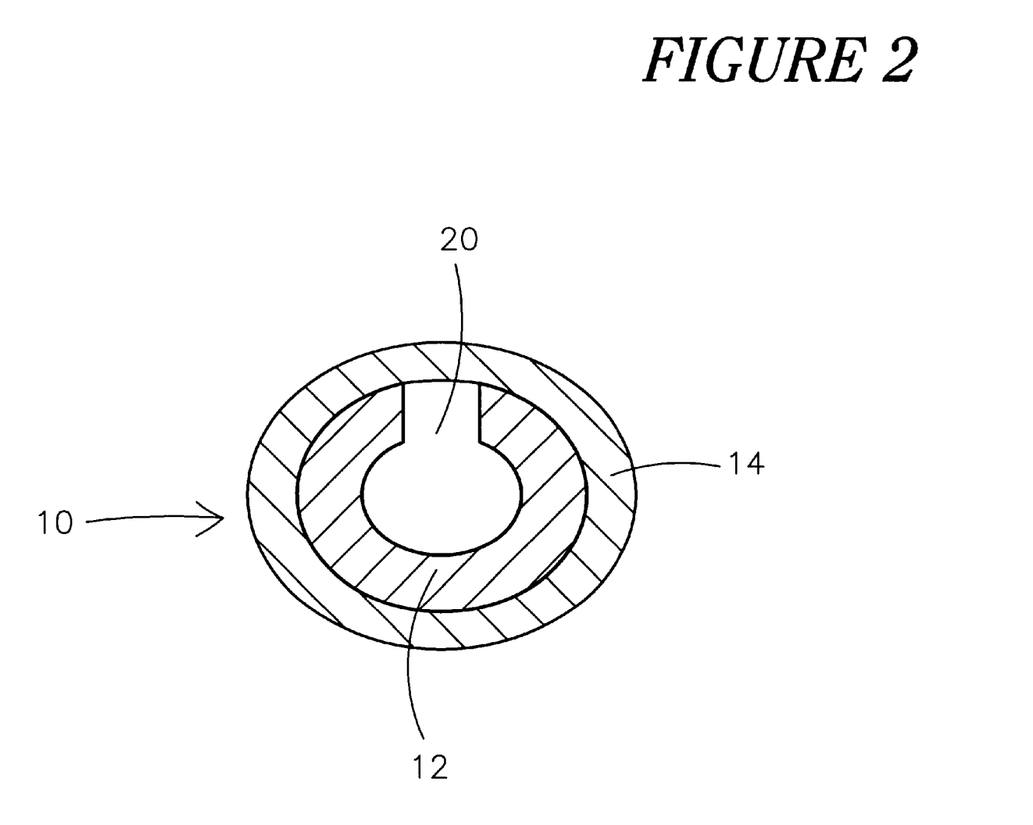
FIG. 2 is a cross-sectional view of the catheter shaft that depicts the wider gap of the taper.

FIG. 2 is a cross-sectional view of catheter shaft 10 from FIG. 1 that depicts the wider gap of variable taper 16. The wider gap can provide increased flexibility of the catheter. Preferably, the wider gap is near the distal end of the catheter. The cross-section of catheter 10 includes elongate support member 12 disposed within sheath 14.

Figure 3:
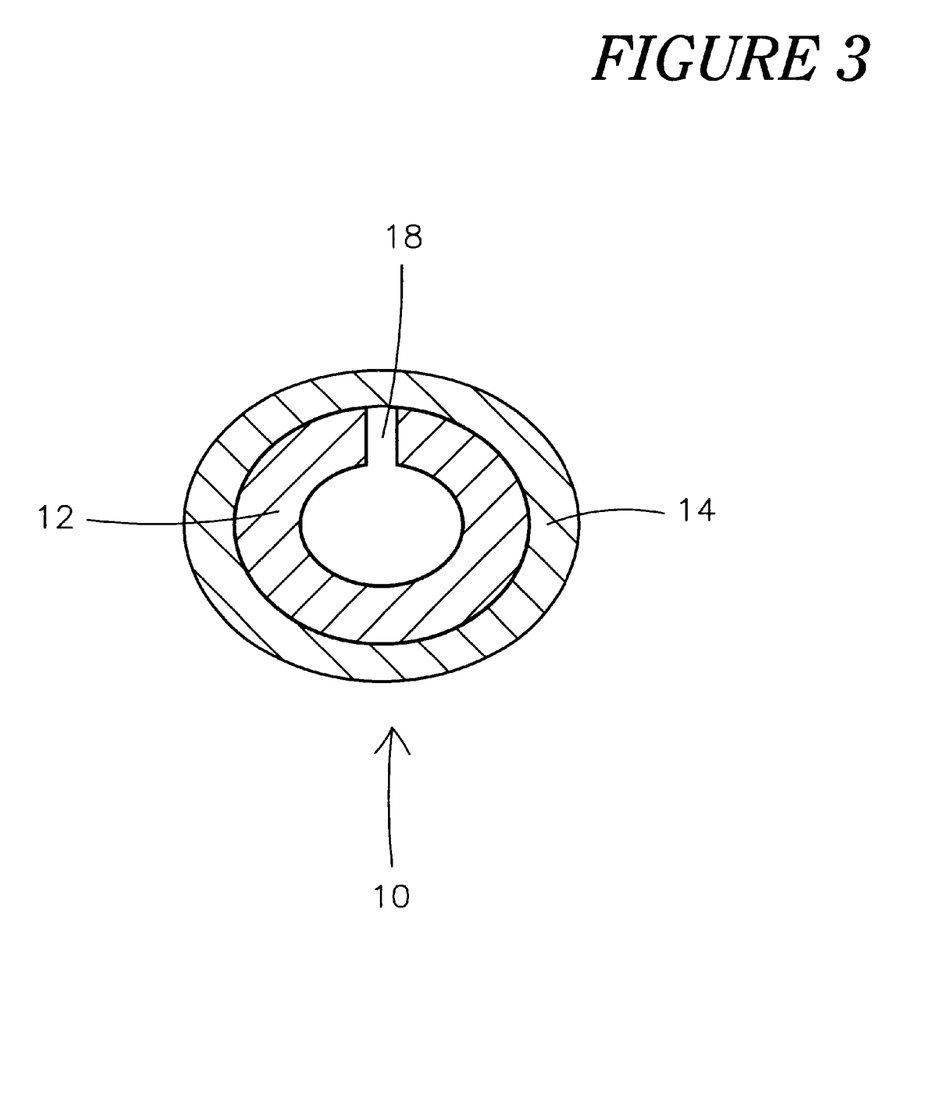
FIG. 3 is a cross-sectional view of the catheter shaft that depicts the narrower gap of the taper.

FIG. 3 is a cross-sectional view of catheter shaft 10 from FIG. 1 that depicts the narrower gap of variable taper 16. The narrower gap may provide less flexibility of the catheter. Preferably, the narrower gap is near the proximal end of the catheter. The cross-section of catheter shaft 10 includes elongate support member 12 disposed within sheath 14.

Figure 4:
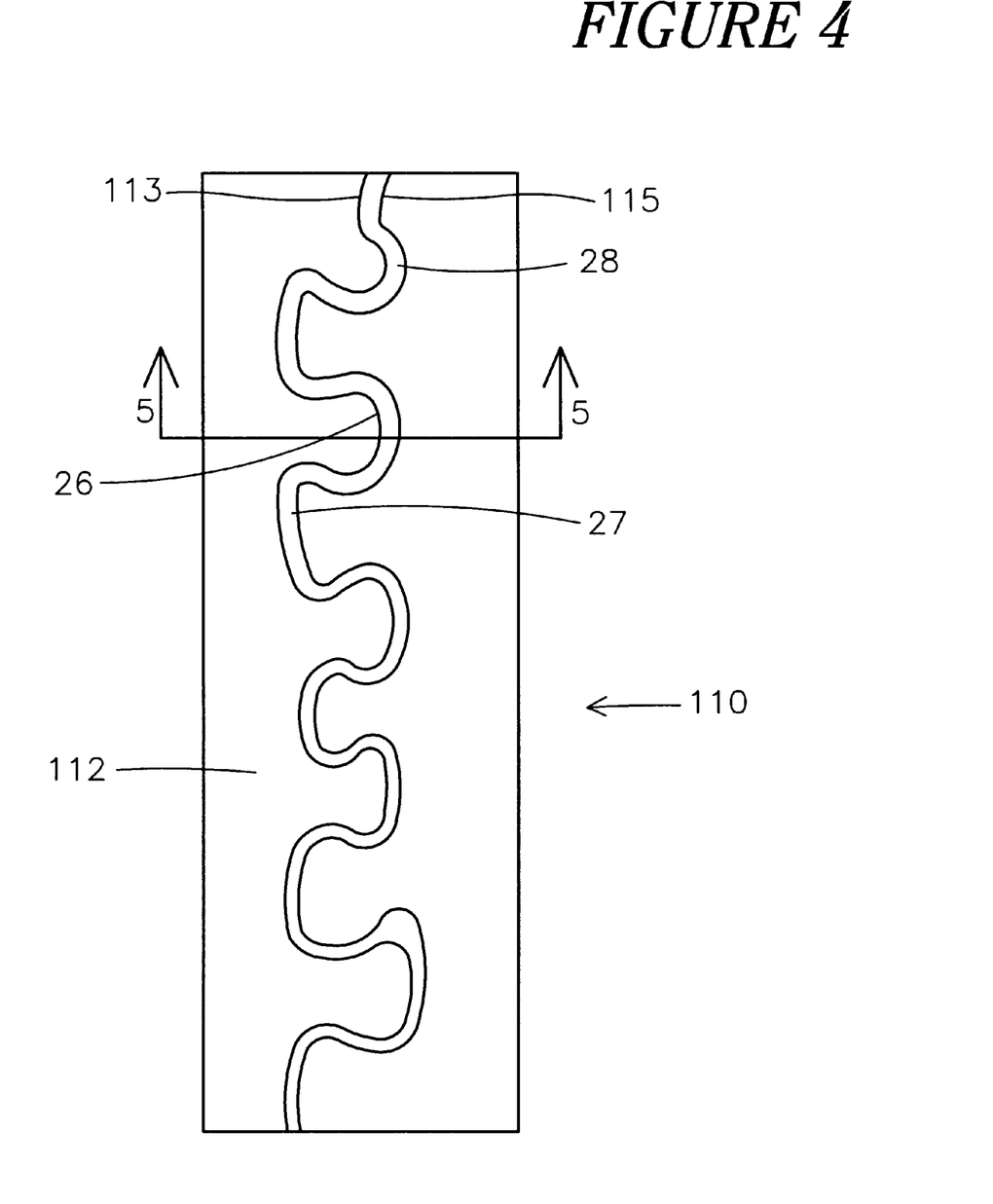
FIG. 4 is a longitudinal view of a catheter shaft with an elongate support member comprising a first projection and a second projection wherein the projections are rounded and interlocking.

FIG. 4 is a longitudinal view of a catheter shaft 110, comprising an elongate support member 112 disposed within a sheath (not shown in FIG. 4, see FIG. 5), a gap 28 defining first edge 113 and second edge 115, a first projection 26 extending from first edge 113, and a second projection 27 extending from second edge 115. Preferably, first projection 26 and second projection 27 are interlocking. By interlocking projections, shaft 110 may retain pushability and torquability while increasing flexibility. A cross-sectional through the elongate support member 12, line 4—4, includes at least one gap 28. Preferably, first projection 26 and second projection 27 overlap.

Altering the shape of gap 28 can enhance desired flexibility changes throughout the catheter. In an exemplary embodiment, first projection 26 and second projection 27 are substantially rounded. For example, rounded projections can vary in size along the longitudinal axis of the elongate support member. A specific example may include larger rounded projections near the proximal end and smaller projections near the distal end. In this example, the smaller projections near the distal end may increase flexibility near the distal end of the catheter shaft.

Additionally, rounded projections can vary in the amount of gap 28 formed between a plurality of interlocking projections. For example, gap 28 between interlocking projections may be uniformly altered in differing embodiments. In this example, catheter shaft 110 could be constructed that has increased gap length between interlocking projections that may result in increased flexibility.

Further, the gaps formed between interlocking projections may vary along the longitudinal axis of the elongate support member. For example, the gap length may be greater near the distal end. This may result in increased catheter shaft flexibility near the distal end of the elongate support member. The ability to alter gap lengths at different points along the longitudinal axis creates countless possible configurations that may each have a beneficial configuration for differing embodiments of the current invention.

Figure 5:
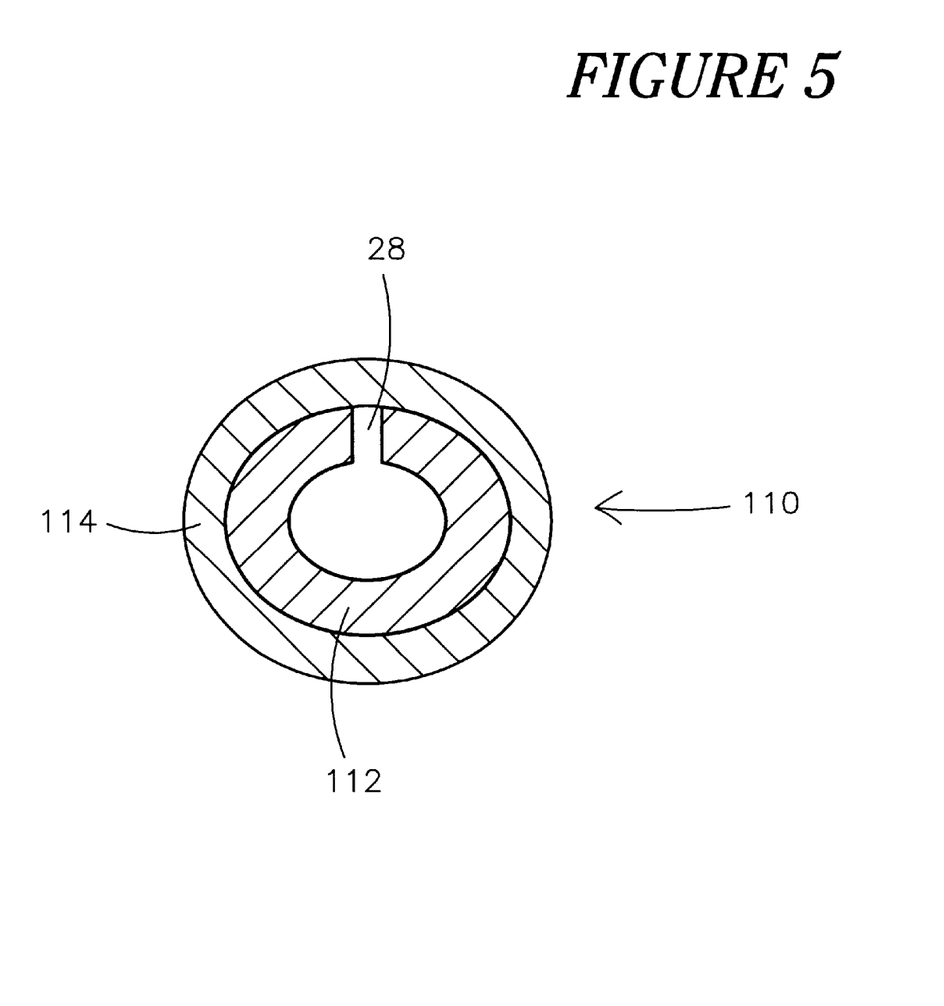
FIG. 5 is a cross-sectional view of the catheter shaft that depicts the gap near the interlocking projections.

FIG. 5 is a cross-sectional view of catheter shaft 110 from FIG. 4 that depicts gap 28. Catheter shaft 110 according to this embodiment of the current invention comprises elongate support member 112 disposed within sheath 114.

Figure 6:
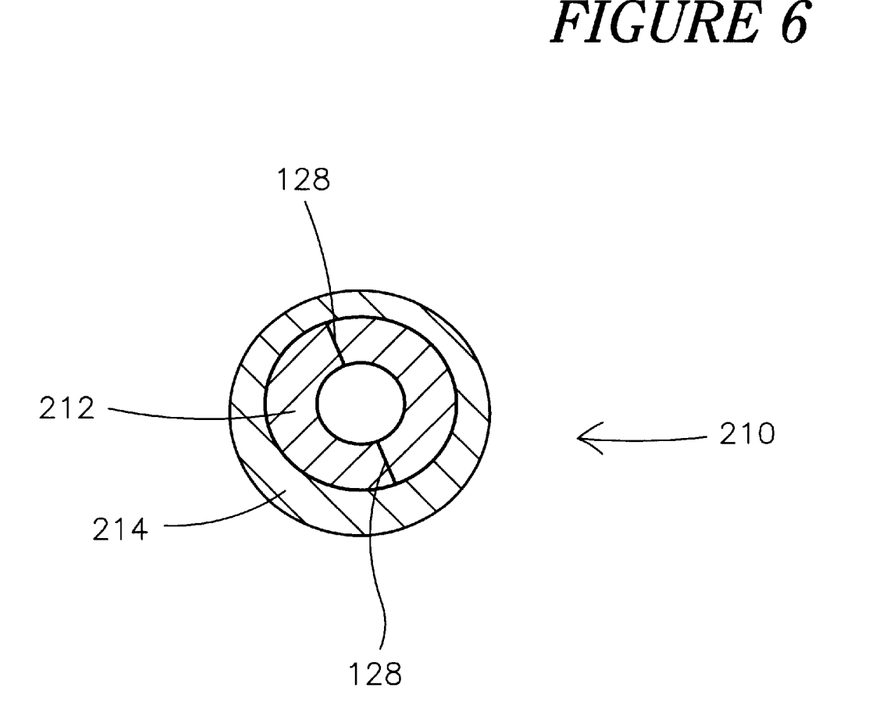
FIG. 6 is an alternate cross-sectional view of the catheter shaft that depicts a minimum gap near the interlocking projections.

FIG. 6 is an alternative cross-sectional view of catheter shaft 110 from FIG. 4 that depicts a minimum gap 128 that approaches zero. A catheter shaft 210 according to this embodiment of the current invention comprises an elongate support member 212 disposed within a sheath 214. By minimizing the gaps it may be possible to control flexibility for multiple embodiments of the current invention.

Additionally, by forming a plurality of gaps, the elongate support member may be divided into more than one piece. This multi-piece configuration may add beneficial properties to the catheter shaft including, but not limited to, increased flexibility, increased kink resistance, pushability, and torquability.

Figure 7:
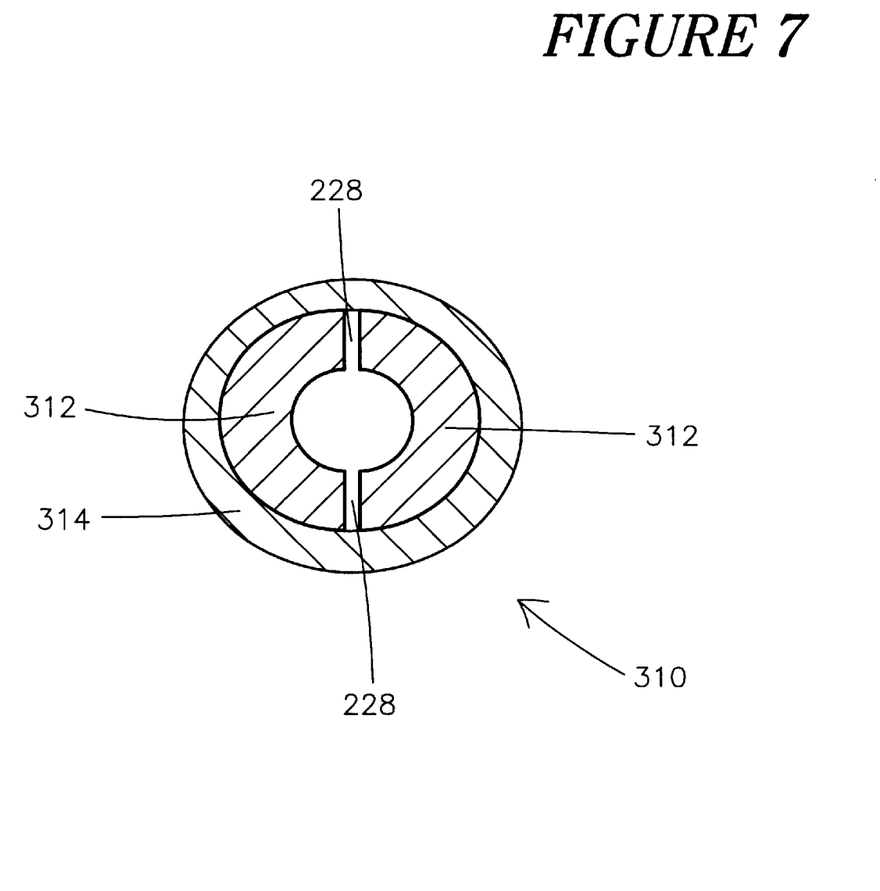
FIG. 7 is an alternate cross-sectional view of the catheter shaft that depicts a gross gap near the interlocking projections.

FIG. 7 is an alternative cross-sectional view of catheter shaft 110 from FIG. 4 that depicts a gross gap 228. A catheter shaft 310 according to this embodiment of the current invention comprises an elongate support member 312 disposed within a sheath 314. By forming larger gaps it may be possible to control flexibility for multiple embodiments of the current invention.

Figure 8:
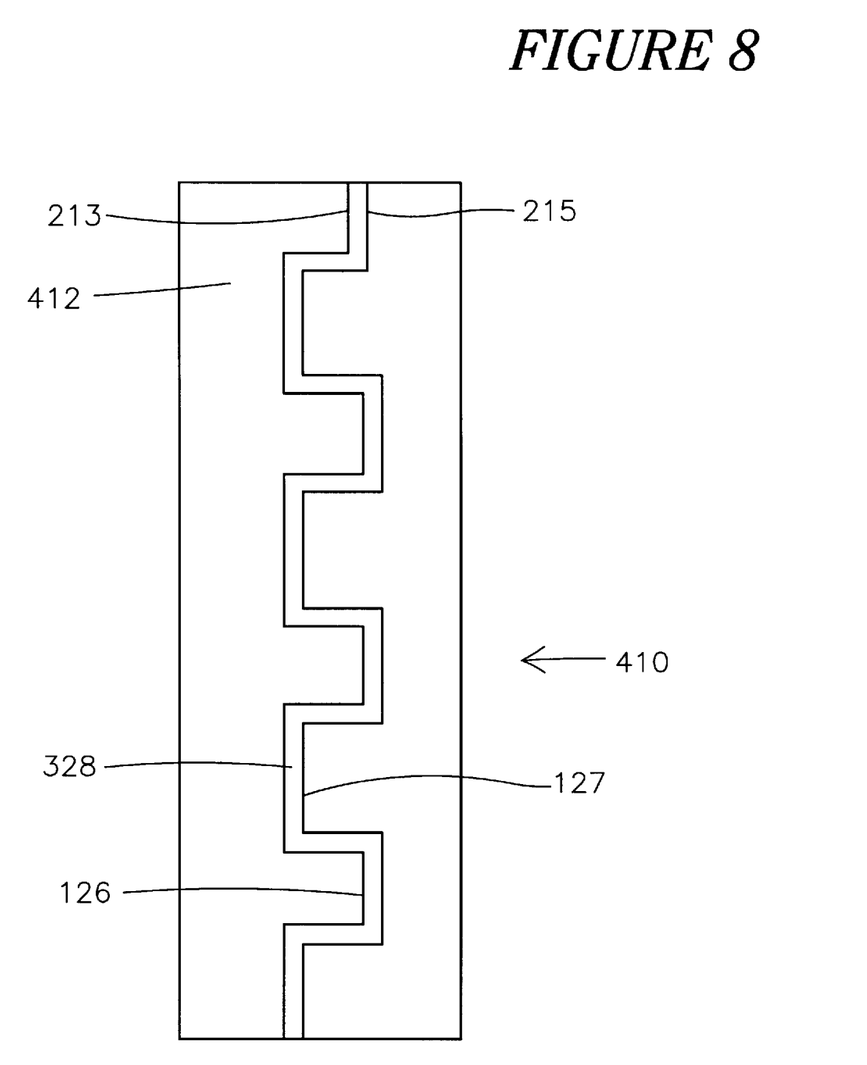
FIG. 8 is a longitudinal view of a catheter shaft with an elongate support member comprising a first projection and a second projection wherein the projections are non-interlocking.

FIG. 8 is a longitudinal view of a catheter shaft 410, comprising an elongate support member 412 disposed within a sheath (not shown), a gap 328 that defines first edge 213 and second edge 215, first projection 126 extending from first edge 213, and second projection 127 extending from second edge 215. The projections could manifest in a multiplicity of shapes according to differing embodiments of the current invention. In multiple embodiments of the current invention, the projections could also have varying size and gap length. Preferably, first projection 126 and second projection 127 overlap.

Altering the shape of the projections can enhance desired flexibility changes throughout the shaft. For example, the projections can vary in size along the longitudinal axis of the elongate support member. A specific example may include larger projections near the proximal end and smaller projections near the distal end. In this example, the smaller projections near the distal end may increase flexibility near the distal end of the catheter.

The projections may also vary in the amount of gap 328 formed between a plurality of surfaces of the elongate support member. For example, gap 328 between surfaces of the elongate support member may be uniformly altered in differing embodiments. In this example, catheter shaft 410 could be constructed that has increased gap length between surfaces that may result in increased flexibility.

Additionally, the gaps formed between surfaces may vary along the longitudinal axis of the elongate support member. For example, the gap length may be greater near the distal end of the shaft. This may result in increased catheter shaft flexibility near the distal end. The ability to alter gap lengths at different points along the longitudinal axis creates countless possible configurations that may each have a beneficial configuration for differing embodiments of the current invention.

Figure 9:
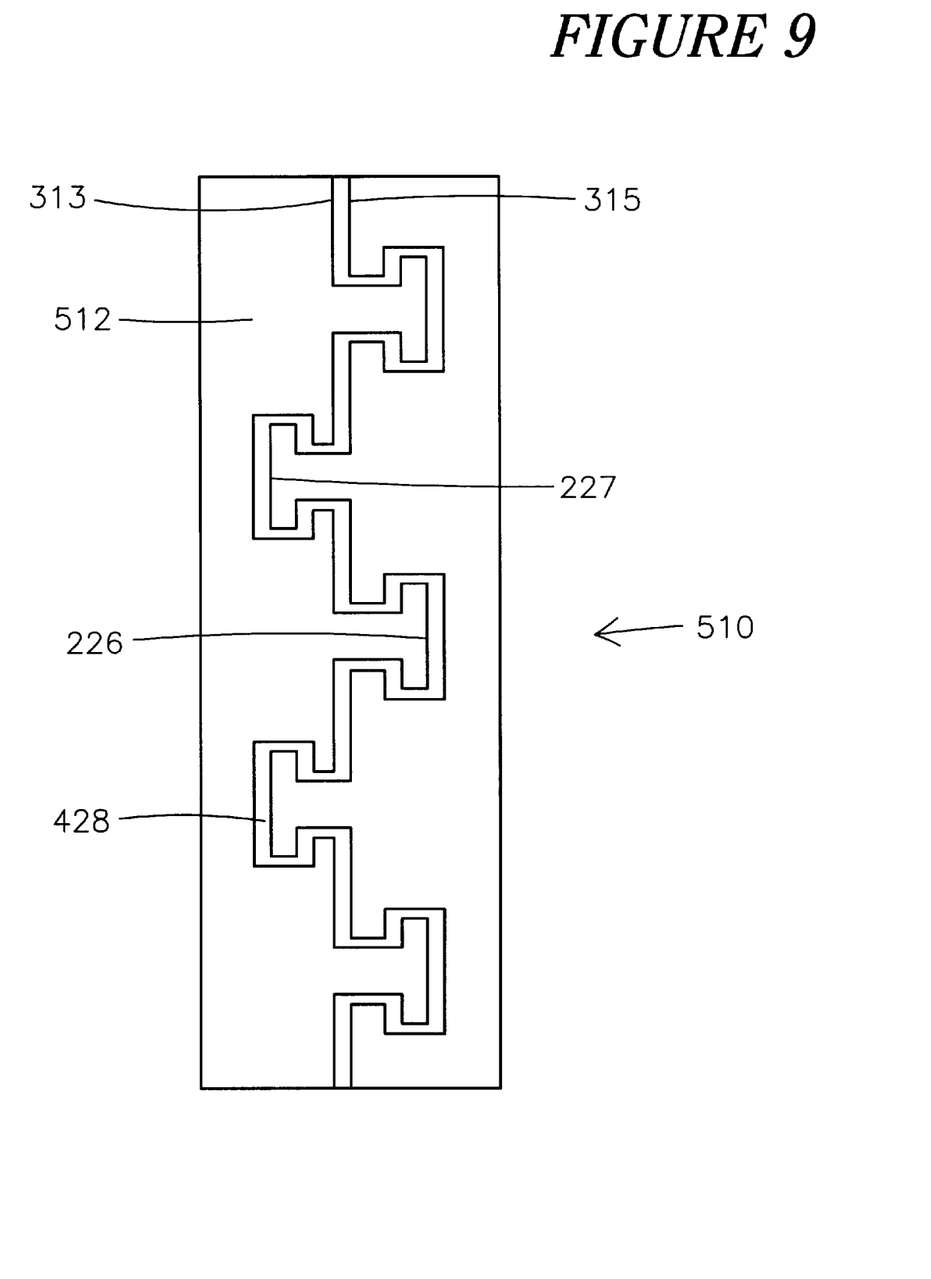
FIG. 9 is a longitudinal view of a catheter shaft with an elongate support member comprising a first projection and a second projection wherein the projections are interlocking.

FIG. 9 is a longitudinal view of a catheter shaft 510, comprising an elongate support member 512 disposed within a sheath (not shown), gap 428 that defines a first edge 313 and second edge 315, first projection 226 extending from first edge 313, and second projection 227 extending from second edge 315. Preferably, first projection 226 and second projection 227 are interlocking. The projections could comprise a multiplicity of shapes according to differing embodiments of the current invention. In multiple embodiments of the current invention, the projections could also have varying size and gap length. Preferably, first projection 226 and second projection 227 overlap.

Altering the shape of the projections can enhance desired flexibility changes throughout the catheter shaft. For example, the projections can vary in size along the longitudinal axis of the elongate support member. A specific example may include larger projections near the proximal end and smaller projections near the distal end. In this example, the smaller projections near the distal end may increase flexibility near the shaft's distal end.

Additionally, the projections can vary in the amount of gap 428 formed between a plurality of surfaces of the shaft. For example, gap 428 between surfaces may be uniformly altered in differing embodiments. In this example, shaft 510 could be constructed that has increased gap length between surfaces that may result in increased flexibility.

Further, the gaps formed between surfaces may vary along the longitudinal axis of the elongate support member. For example, the gap length may be greater near the distal end. This may result in increased catheter shaft flexibility near the distal end of the catheter shaft. The ability to alter gap lengths at different points along the longitudinal axis creates countless possible configurations that may each have a beneficial configuration for differing embodiments of the current invention.

Figure 10:
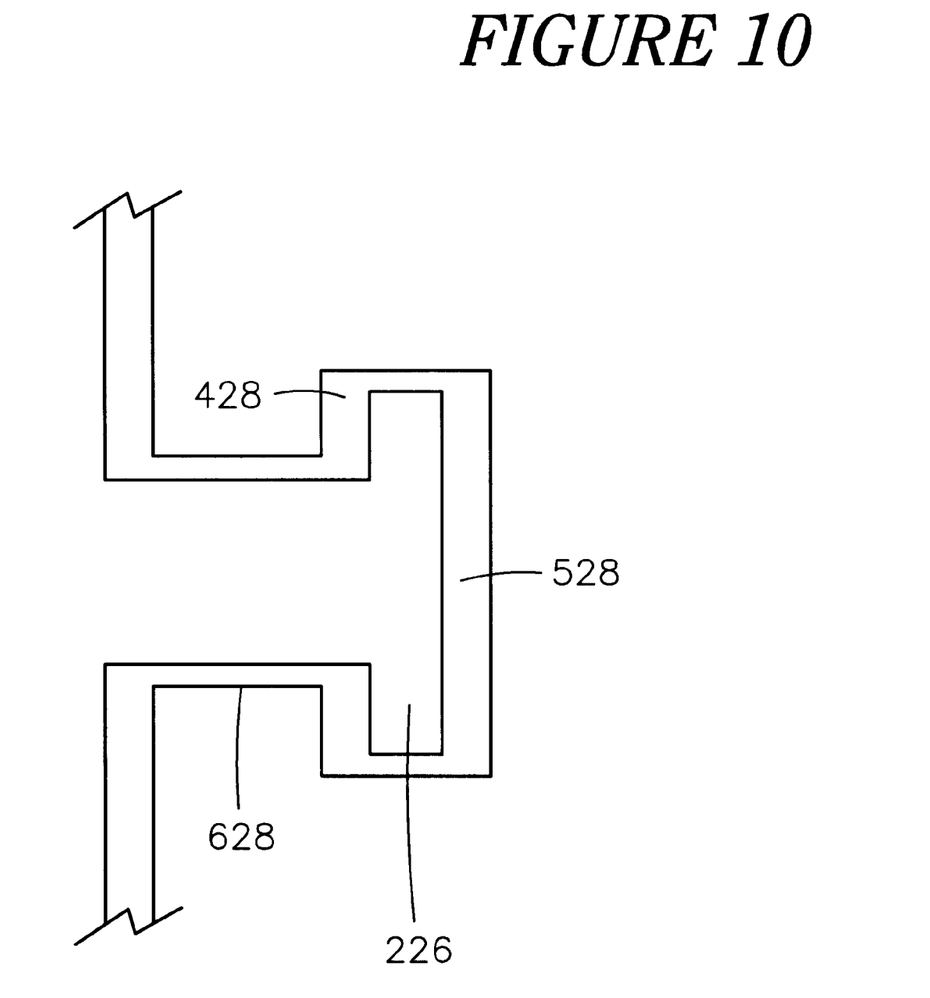
FIG. 10 is an enlarged longitudinal view the first projection.

FIG. 10 is an enlarged longitudinal view of first projection 226 that wherein it has differing gap lengths. The gap length can be varied along particular surfaces of a given projection. For example, a projection may have a relatively longer gap 528 in the longitudinal direction (along the longitudinal axis) of the catheter shaft and a relatively shorter gap 628 in the direction perpendicular to the longitudinal axis of the shaft. In this example, the catheter shaft may have increased circumferential flexibility while allowing little axial movement. Multiple embodiments of the current invention can be derived that incorporate varied gaps between surfaces of projections. Similar alterations can be derived for non-interlocking or rounded projections.

Figure 11:
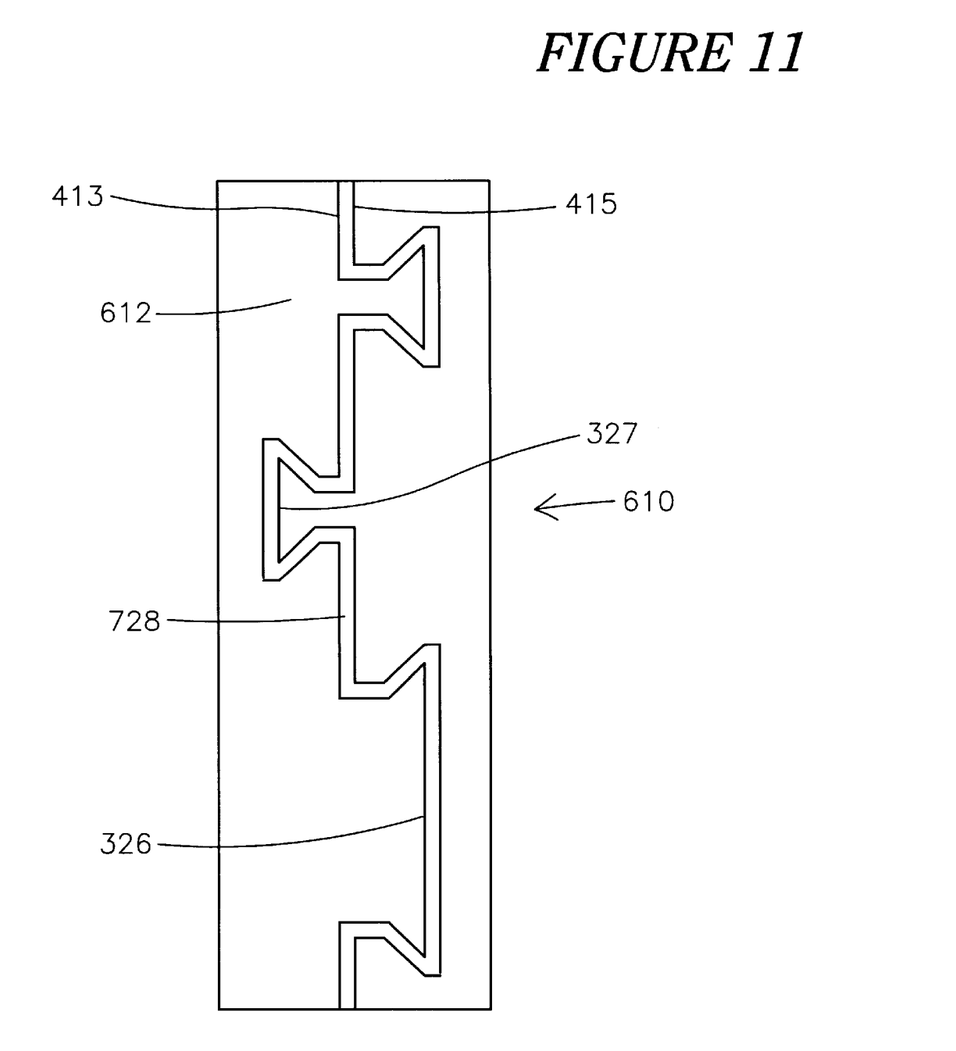
FIG. 11 is a longitudinal view of a catheter shaft with an elongate support member comprising a first projection and a second projection wherein the projections are of differing shapes.

FIG. 11 is a longitudinal view of a catheter shaft 610, comprising an elongate support member 612 disposed within a sheath (not shown), a gap 728 defining first edge 413 and second edge 415, a first projection 326 extending from first edge 413, and a second projection extending from second edge 415. In multiple embodiments of the current invention, the projections could also have varying size and gap 728 length as illustrated above. Further, multiple embodiments can be derived that incorporate varied gaps 728 between surfaces of projections. Similar alterations can be derived for non-interlocking modified projections of differing shapes. Preferably, first projection 326 and second projection 327 overlap.

The projections can vary in the amount of gap 728 formed between a plurality of surfaces of the elongate support member. For example, gap 728 between surfaces may be uniformly altered in differing embodiments. In this example, shaft 610 could be constructed that has increased gap length between surfaces that may result in increased flexibility.

Further, the gaps formed between surfaces may vary along the longitudinal axis of the elongate support member. For example, the gap length may be greater near the distal end. This may result in increased catheter shaft flexibility near the distal end of the catheter shaft. The ability to alter gap lengths at different points along the longitudinal axis creates countless possible configurations that may each have a beneficial configuration for differing embodiments of the current invention.

Figure 12:
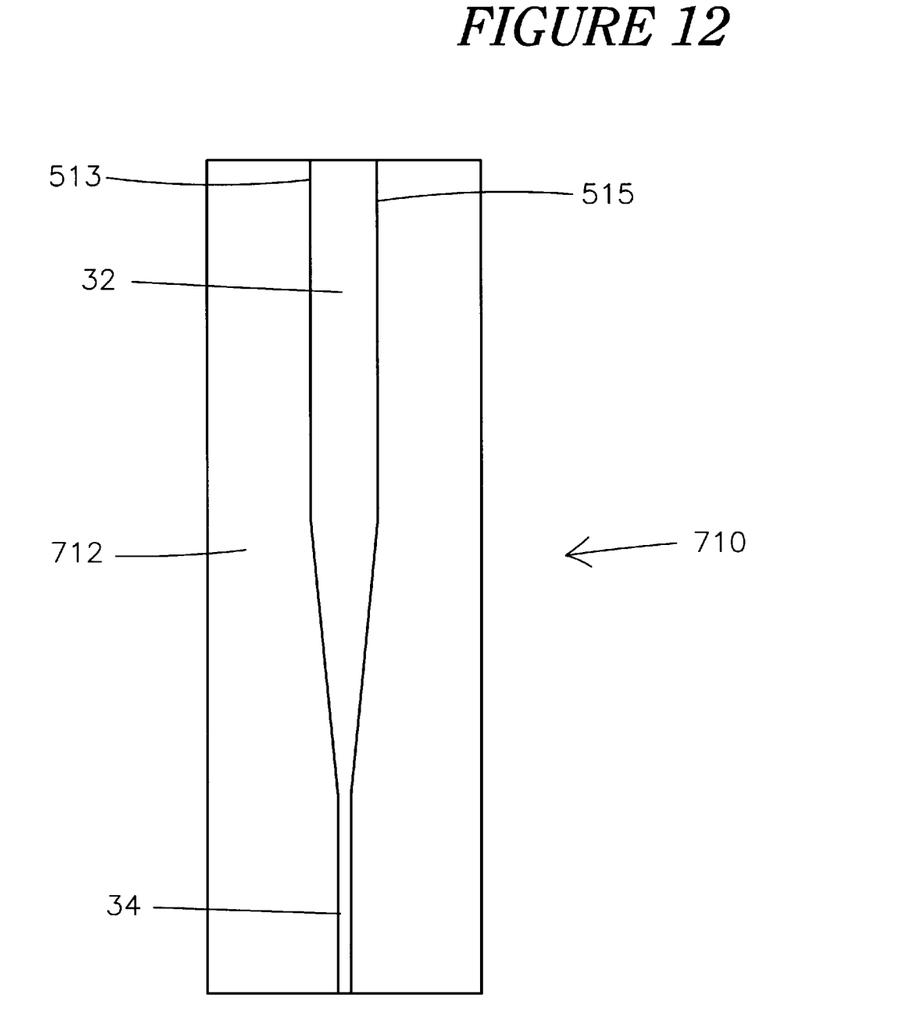
FIG. 12 is a longitudinal view of a catheter shaft with an elongate support member comprising a first edge and a second edge, wherein the gap defines both a tapered and a non-tapered region.

FIG. 12 is a longitudinal view of a catheter shaft 710, comprising an elongate support member 712 disposed within a sheath (not shown), and a taper 32 that defines first edge 513 and second edge 515. According to a preferred embodiment, taper 32 comprises a tapered 32 and a non-tapered region 34. By introducing both tapered 32 and non-tapered region 34, the level of flexibility can vary between proximal and distal ends. For example, the non-tapered region may result in a less flexible region near the proximal end of the catheter and the taper may result in a gap that is greater near the distal end of the catheter shaft. This could result in greater flexibility near the distal end of the catheter.

Elongate support member 712 may further comprise a variable taper as is FIG. 1. A variable taper comprises a narrower gap and a wider gap. By introducing a variable taper, the level of flexibility may vary between proximal and distal points along the elongate support member. For example, the taper may result in a gap that is greater near the distal end of the shaft. This could result in greater flexibility near the distal end of the catheter.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A catheter shaft, comprising:
   an elongate support member having a proximal end, a distal end, and a longitudinal axis;

at least one gap within the elongate support member that defines a first edge and a second edge;

a first projection defined by the first edge;

a second projection defined by the second edge;

wherein the first projection and the second projection overlap; and a sheath disposed about the elongate support member.

2. The catheter shaft in accordance with claim 1, wherein the first projection and the second projection interlock.

3. The catheter shaft in accordance with claim 1, wherein the first projection and the second projection are non-interlocking.

4. The catheter shaft in accordance with claim 1, wherein the first projection is substantially rounded.

5. The catheter shaft in accordance with claim 1, wherein the first projection and the second projection comprise differing shapes.

6. The catheter shaft in accordance with claim 1, wherein the gap is formed by cutting.

7. The catheter shaft in accordance with claim 1, wherein the elongate support member comprises a polymer.

8. The catheter shaft in accordance with claim 1, wherein the elongate support member comprises stainless steel.

9. The catheter shaft in accordance with claim 1, wherein the elongate support member comprises nickel alloy.

10. The catheter shaft in accordance with claim 1, wherein the elongate support member comprises nickel titanium alloy.

11. The catheter shaft in accordance with claim 1, wherein the sheath comprises polyether-ether ketone.

12. The catheter shaft in accordance with claim 1, wherein the sheath comprises polyimide.

13. The catheter shaft in accordance with claim 1, wherein the sheath comprises polyphenylene sulfide.

14. The catheter shaft in accordance with claim 1, wherein the sheath comprises perfluoro(propyl vinyl ether).

* * * * *